US010371697B2

(12) United States Patent
Ibach et al.

(10) Patent No.: US 10,371,697 B2
(45) Date of Patent: Aug. 6, 2019

(54) METHOD OF MANUFACTURING UNI- AND NO-CODE TEST STRIPES

(71) Applicant: Roche Diabetes Care, Inc., Indianapolis, IN (US)

(72) Inventors: Alexander Ibach, Buehl (DE); Yilmaz Isgoeren, Ludwigshafen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 15/216,765

(22) Filed: Jul. 22, 2016

(65) Prior Publication Data
US 2016/0327547 A1 Nov. 10, 2016

Related U.S. Application Data

(63) Continuation of application No. PCT/EP2015/051199, filed on Jan. 22, 2015.

(30) Foreign Application Priority Data

Jan. 24, 2014 (EP) ..................................... 14152464

(51) Int. Cl.
*G01N 21/75* (2006.01)
*G01N 33/52* (2006.01)
(Continued)

(52) U.S. Cl.
CPC ........... *G01N 33/526* (2013.01); *C12Q 1/006* (2013.01); *G01N 21/78* (2013.01); *G01N 21/8483* (2013.01); *G01N 33/66* (2013.01)

(58) Field of Classification Search
CPC ...... G01N 33/526; G01N 33/66; G01N 21/78; G01N 21/8483; C12Q 1/006
See application file for complete search history.

(56) References Cited

U.S. PATENT DOCUMENTS 3,992,158 A 11/1976 Przybylowicz et al.
4,815,860 A * 3/1989 Deuse ..................... B28C 7/062
366/10
(Continued)

FOREIGN PATENT DOCUMENTS

DE 196 29 656 A1 1/1998
DE 196 29 657 A1 1/1998
(Continued)

OTHER PUBLICATIONS

Pohl, Markus et al., "Herstellung stabiler Dispersionen aus pyrogener Kieselsaure". English-language translation. Chemie Ingenieur Technik 2005, 77. No. 3. 10 pages.
(Continued)

*Primary Examiner* — Dennis White
(74) *Attorney, Agent, or Firm* — Woodard, Emhardt, Henry, Reeves & Wagner, LLP

(57) ABSTRACT

The present invention pertains to the field of manufacture of diagnostic test elements. Specifically, the invention relates to a diagnostic test element for determining an analyte comprised in a body fluid sample, said test element comprising at least one test field with at least one detection layer and at least one separation layer, wherein said at least one separation layer comprises dispersed $SiO_2$ in an amount of about 1.0 to 1.6 $g/m^2$. The invention also relates to a coating composition being capable of forming a separation layer on a diagnostic test element of the present invention described above. Moreover, provided is a method for the manufacture of the diagnostic test element as well as the use of the diagnostic test element for determining the amount of an analyte, preferably, glucose, in a sample of a subject.

13 Claims, 12 Drawing Sheets

(51) Int. Cl.
*G01N 21/78* (2006.01)
*G01N 21/84* (2006.01)
*C12Q 1/00* (2006.01)
*G01N 33/66* (2006.01)

(56) References Cited

U.S. PATENT DOCUMENTS

| | | |
|---|---|---|
| 4,966,855 A | 10/1990 | Deneke et al. |
| 5,652,148 A | 7/1997 | Doshi et al. |
| 5,846,837 A | 12/1998 | Thym et al. |
| 6,036,919 A | 3/2000 | Thym et al. |
| 6,696,024 B1 | 2/2004 | Leichner et al. |
| 7,238,534 B1 | 7/2007 | Zimmer |
| 8,574,514 B2 | 11/2013 | Petrich et al. |
| 2003/0031592 A1 | 2/2003 | Knappe |
| 2005/0130296 A1 | 6/2005 | Pisharody et al. |
| 2006/0003397 A1 | 1/2006 | Knappe et al. |
| 2008/0213808 A1 | 9/2008 | Knappe |
| 2009/0145775 A1 | 6/2009 | Chu et al. |
| 2011/0179970 A1 | 7/2011 | Zschunke et al. |
| 2012/0040386 A1* | 2/2012 | Knappe ............... B01L 3/5027 435/14 |
| 2012/0276565 A1 | 11/2012 | Roedel et al. |
| 2015/0018441 A1* | 1/2015 | Wang .................... C08K 5/053 521/76 |

FOREIGN PATENT DOCUMENTS

| | | |
|---|---|---|
| EP | 0 167 973 A1 | 1/1986 |
| EP | 0 821 234 B1 | 1/1998 |
| EP | 1 035 919 B1 | 9/2000 |
| EP | 1 035 920 B1 | 9/2000 |
| EP | 2 360 120 A1 | 8/2011 |
| JP | H10-078430 A | 3/1998 |
| JP | 2012-508372 A1 | 4/2012 |
| WO | WO 2010/053206 A1 | 5/2010 |
| WO | WO 2011/020856 A1 | 2/2011 |

OTHER PUBLICATIONS

International Patent Application No. PCT/EP2015/051199 International Preliminary Report on Patentability dated Apr. 21, 2016, 12 pages.
International Patent Application No. PCT/EP2015/051199 International Search Report dated Jul. 30, 2015.
International Patent Application No. PCT/EP2015/051199 Written Opinion dated Jul. 30, 2015.
Pohl, Markus et al., "Herstellung stabiler Dispersionen aus pyrogener Kieselsaure". Chemie Ingenieur Technik 2005, 77. No. 3. 5 pages.

* cited by examiner

A

B

C

D

E

F

A

B

A

B

C

D

E

F

A

B

C

D

E

F

A

B

METHOD OF MANUFACTURING UNI- AND NO-CODE TEST STRIPES

CROSS-REFERENCE TO RELATED APPLICATION

This application is a continuation of International Patent Application No. PCT/EP2015/051199, filed Jan. 22, 2015, which claims the benefit of European Patent Application No. 14152464.5, filed Jan. 24, 2014, the entire disclosures of which are hereby incorporated by reference.

BACKGROUND

The present invention pertains to the field of manufacture of diagnostic test elements. Specifically, the invention relates to a diagnostic test element for determining an analyte comprised in a body fluid sample, said test element comprising at least one test field with at least one detection layer and at least one separation layer, wherein said at least one separation layer comprises dispersed $SiO_2$ in an amount of about 1.0 to 1.6 $g/m^2$. The invention also relates to a coating composition being capable of forming a separation layer on a diagnostic test element of the present invention described above. Moreover, provided is a method for the manufacture of the diagnostic test element as well as the use of the diagnostic test element for determining the amount of an analyte, preferably, glucose, in a sample of a subject.

In the prior art, numerous diagnostic test elements are known which can be used for detecting an analyte in a sample of a body fluid. The said analyte can be, for example, a metabolite such as glucose. Qualitative and/or quantitative detection of the analyte can be carried out. Known analytes are, for example, glucose, more particularly blood glucose, uric acid, ethanol, and/or lactate. Other types of analytes are also alternatively or additionally detectable. The body fluid can be, for example, whole blood, blood plasma, interstitial fluid, saliva, urine, or other types of body fluids. The invention will now, without restricting further possible embodiments, be described essentially with reference to the detection of glucose in whole blood.

Diagnostic test elements, in principle, comprise at least one detection reagent for the qualitative and/or quantitative detection of the analyte. A detection reagent is to be generally understood to mean a chemical substance or a mixture of chemical substances which, in the presence of the at least one analyte, changes at least one detectable property, more particularly a physically and/or chemically detectable property. Preferably, this property change occurs specifically only in the presence of the at least one analyte to be detected, but not in the presence of other substances. However, in practice, it is possible to tolerate an unspecific property change within certain limits, in the presence of other chemical substances whose presence in the sample of the body fluid is generally unlikely and/or which are present at only a very low concentration.

The at least one property change can be, for example, the change in an optically detectable property, more particularly a color change. Examples of diagnostic test elements having optical detection reagents are well known in the prior art. For example, DE 196 29 656 A1, DE 196 29 657 A1, WO 2010/052306 or EP 0 821 234 B1 describe diagnostic test supports for determining an analyte from whole blood by means of a reagent system which is present in the support and which includes a color formation reagent. Such a diagnostic test support comprises a test field with a sample loading side, onto which the sample is added, and a detection side, on which an optically detectable change occurs as a result of the reaction of the analyte with the reagent system. The test field is configured such that the erythrocytes present in the sample do not reach the detection side. Furthermore, the test field has a transparent slide and a first film layer and also a second film layer applied to the first film layer. The first layer located on the transparent slide is in a moist state and thereby exhibits considerably less light scattering than the second layer lying over it. The first film layer comprises a filler whose refractive index is close to the refractive index of water, whereas the second layer contains a pigment having a refractive index of at least or even >2.0, more particularly of at least 2.2, at a concentration of at least 25% by weight or even more than 25% by weight, based on the dried second layer. For example, the first layer can comprise a sodium aluminum silicate as filler.

However, in practice, the test elements known from the prior art, more particularly test elements having at least one test field, have disadvantages and technical challenges. Since the composition of the film layers may vary from batch to batch, variations may also occur during measurements, e.g., due to remission variation. Currently, batch specific calibration curves are provided as so called "ROM Keys" in electronic format in order to allow for a precise measurement of the analyte. However, it is a rather cumbersome measure for the practitioner to apply an individual calibration curve for each and every batch. Moreover, there is a risk for using wrong calibration curves due to confusions.

A possibility which is currently realized to avoid confusions and additional work for exchanging the ROM-Key comprising the calibration curve is storing the calibration information for the diagnostic test elements on each element or on a magazine comprising a plurality of test elements from the same batch. However, this measure is cost intensive and requires extra production steps since each test element needs to be labeled by, e.g., a bar code or test elements of one batch need to be stored in a bar code labeled magazine.

However, there is a need for less cost intensive measures for safeguarding measurement qualities of the diagnostic test elements which can be realized without the need for additional production steps.

SUMMARY

The technical problem underlying the present invention can be regarded as the provision of means and methods for complying with the aforementioned needs. The said technical problem is solved by the embodiments characterized in the claims and herein below.

Accordingly, the present invention relates to a diagnostic test element for determining an analyte comprised in a body fluid sample, said test element comprising at least one test field with at least one detection layer and at least one separation layer, wherein said at least one separation layer comprises dispersion-saturated solid components and $SiO_2$ in an amount of about 1.0 to 1.6 $g/m^2$.

The term "diagnostic test element" as used herein refers to a device comprising at least one test field for sample application and analysis. Accordingly, the said test field comprises reagents for analyzing a sample for the presence or absence of the analyte. Typically, such reagents comprise one or more detection agents which recognize the presence of the analyte in an applied sample and which are adapted to go through at least one detectable change of a physical and/or, chemical property in the presence of the analyte to be determined. Typically, optical chances are elicited in the presence of the analyte although other changes such as chemical changes or electrochemical changes are also conceivable.

Details on the principles underlying such test elements and the manufacture thereof can be found in DE 196 29 657 A1, DE 196 29 656 A1, or EP 0 821 234 B1 which are herewith incorporated by reference. Further test elements envisaged in accordance with the present invention are those disclosed in EP 1 035 919 B1 or EP 1 035 920 B1, the respective disclosure content of which is herewith incorporated by reference. The layers of the diagnostic test element according to the invention are, in an aspect, film layers and are produced from dispersions or emulsions of polymeric film formers. Dispersion film formers contain microscopic polymer particles which are insoluble in the carrier liquid (usually water) and are finely dispersed in the carrier liquid. If the liquid is removed by evaporation during film formation then the particles come closer and finely touch one another. The large forces which occur in this process and the gain in surface energy which accompanies the film formation result in the particles growing into a substantially closed film layer. Alternatively it is also possible to use an emulsion of the film former in which this is dissolved in a solvent. The dissolved polymer is emulsified in a carrier liquid which is immiscible with the solvent. Polyvinyl esters, polyvinyl acetates, polyacrylic esters, polymethacrylic acid, polyvinyl amides, polyamides and polystyrene are particularly suitable as polymers for such film formers. In addition to homopolymers mixed polymerizates are also suitable such as of butadiene, styrene or maleic acid ester.

In an embodiment, dispersion and/or saturated dispersion is achieved by one of the methods as described elsewhere herein or by a method known to the skilled person, e.g. from Pohl et al. (2005), Chemie Ingenieur Technik 77(3): 258-262 and from EP 2 360 120 A1. Also in an embodiment, the degree of dispersion is determined by one of the methods as described elsewhere herein or by a method known to the skilled person, e.g. from the aforesaid references Pohl et al. and EP 2 360 120 A1. In a particular embodiment, dispersion saturation is determined by determining size distribution of the distributed particles, in particular by laser diffraction measurement, or by characterizing the dispersion using a dispersion analyzer, in particular a LUMiSizer® (LUM GmbH, Berlin).

It follows from the above that the diagnostic test element of the present invention may be used for determining the presence or absence or amount of an analyte. The term "amount" as used herein refers to the absolute or relative amount of analyte present in a sample applied to the diagnostic test element. A relative amount preferred according to the present invention is the concentration, i.e. the amount in relation to the volume.

The term "body fluid sample" as used herein, in principle, encompasses all types of body fluids, such as blood and blood derivatives, urine, saliva, lymph, liquor, tears, etc. The body fluid sample shall be known or suspected to comprise the analyte to be determined. Body fluids known to comprise a plurality of diagnostically relevant analytes are blood including whole blood, plasma and serum, urine, saliva, liquor, synovial liquid, and sudor. Typically, blood and its derivatives plasma and serum are envisaged, however, in accordance with the present invention as body fluid samples.

In particular, the analyte which shall be determined in accordance with the present invention is glucose. Accordingly, typical detection agents for determining glucose as an analyte are enzymes such as glucose dehydrogenases. Typically, FAD-, NAD+-, or PQQ-dependent glucose dehydrogenases or mutants thereof including those disclosed in WO2011/020856 are to be used. Furthermore, the detection agents may comprise enzymes which are required for the transfer of redox equivalents obtained from the glucose dehydrogenases such as diaphorases and, in particular, a lipoamide deydrogenase or a NADH dehydrogenase or an enzymatically active mutant thereof. Moreover, the detection reagents can, alternatively or additionally, comprise one or more mediators, i.e., substances capable of transferring electrical charges from one substance to another. More particularly, mediators can be used which are suitable for electron transfer. For example, this substance can be nitrosoaniline. Furthermore, the detection reagents can, again alternatively or additionally, comprise at least one indicator. An indicator can be understood to be a substance which as such can change at least one property which can be detected, depending on in which form this substance is present. For example, substances can be used which, in an oxidized and a reduced form, can have different optical properties, for example different colors.

Alternatively or additionally, the indicator can comprise a substance which, in different charge states, has different optical properties, for example different color properties. In particular, an indicator envisaged in accordance with the present invention is 2,18-phosphoromolybdic acid, hereinafter also referred to as phosphoromolybdic acid. Thus, in general, the one or more detection reagents can be understood to be a single substance or a mixture of substances, for example, as explained above, a mixture of at least one enzyme, at least one mediator, and at least one indicator. Such detection reagents are known in principle from the prior art, for example from the prior art described above.

The term "test field" as referred to in accordance with the present invention relates to an area of the diagnostic test element which can be used for sample application and/or analysis. The test element may be part of the diagnostic test element or may be the diagnostic element. In principle, the test field has a sample application side onto which the body fluid sample is applied and a detection side which allows for detection of a change in an optical and/or chemical property when the analyte reacts with the reaction agent(s). The test field has at least one detection layer comprising the detection reagent(s). A system having a single detection layer can be used, or multiple detection layers can be used which can be applied on top of one another, directly or by interposing one or more further layers. However, particular preference is given to a system having only a single detection layer. A layer is to be understood in the context of the present invention to mean in general an element in which a layer material is applied flat to a support element or is formed as a freestanding film. The layer can, but need not necessarily, be closed, but can have, for example, openings as well. However, particular preference is given to, as will be more particularly developed below, a substantially uniform, preferably porous but homogenously coated, homogeneous embodiment of the detection layer having a homogeneous layer thickness. The layer thickness, i.e., the average thickness of the detection layer, is preferably 3 to 60 µm, more particularly 5 to 15 µm, for example 8 µm.

According to the invention the test field comprises a transparent foil onto which a first film layer (i.e. the detection layer) and a second film layer (i.e. the separation layer) are applied resting on top of one another in this order. It is important that the first layer located on the transparent foil scatters light considerably less than the overlying second layer. The non-coated side of the transparent foil is referred to as the detection side and the side of the second layer which is opposite to the side with which the second layer rests on the first is referred to as the sample application side. As transparent foils, plastic foils come into consideration being impermeable to liquid. Polycarbonate foil has proven to be particularly suitable.

The term "detection layer" (or "first layer") as used herein refers to a film layer in the test field which comprises the reaction reagent(s) as specified above. Moreover, the said layer shall also comprise coating compounds which contain polymeric film formers, swelling agents and weakly light scattering fillers or no fillers at all. Weakly light fillers are those in accordance with the present invention whose refractive index is near to the refractive index of water. Silicone dioxide, silicates and aluminum silicates have proven to be particularly suitable for this purpose.

The term "separation layer" (or "second layer") as used herein refers to a film layer in the test field which comprises dispersion-saturated solid components. Typically, said dispersion-saturated solid components in the separation layer of the diagnostic test element according the present invention have been obtained by dispersing the solid components in a coating composition forming the separation layer until a maximum is reached such that no further increase in the amount of dispersed solid components can be observed (plateau stage). How to obtain such dispersed coating compositions and layers is well known in the art and described elsewhere herein in more detail.

Moreover, the separation layer shall comprise $SiO_2$ in an amount of about 1.0 to 1.6 $g/m^2$. The term "about" in the context of the present invention encompasses variations of the indicated value of +/−15%, +/−10%, +/−5%, +/−3%, +/−2% or +/−1% and the indicated value itself. In some embodiments the separation layer shall comprise $SiO_2$ in an amount of about 1.2 to 1.5 $g/m^2$. In some embodiments the separation layer shall comprise $SiO_2$ in an amount of about 1.3 to 1.4 $g/m^2$. In some embodiments the separation layer shall comprise $SiO_2$ in an amount of about 1.4 $g/m^2$. More typically, the separation layer may comprise $SiO_2$ in an amount of about 1.00 to 1.05 $g/m^2$, 1.00 to 1.10 $g/m^2$, 1.00 to 1.15 $g/m^2$, 1.00 to 1.20 $g/m^2$, 1.00 to 1.25 $g/m^2$, 1.00 to 1.30 $g/m^2$, 1.00 to 1.35 $g/m^2$, 1.00 to 1.40 $g/m^2$, 1.00 to 1.45 $g/m^2$, 1.00 to 1.50 $g/m^2$, or 1.00 to 1.55 $g/m^2$ or about 1.05 to 1.60 $g/m^2$, 1.10 to 1.60 $g/m^2$, 1.15 to 1.60 $g/m^2$, 1.20 to 1.60 $g/m^2$, 1.25 to 1.60 $g/m^2$, 1.30 to 1.60 $g/m^2$, 1.35 to 1.60 $g/m^2$, 1.40 to 1.60 $g/m^2$ or 1.45 to 1.60 $g/m^2$. Further, the separation layer requires a swelling agent and in any case at least one pigment scattering light strongly. In addition the second layer can also contain non-porous fillers as well as porous fillers. By adding a swelling agent that swells well (i.e. a substance which increases its volume when it takes up water) one does not only obtain layers which can be penetrated relatively rapidly by sample liquid but have good erythrocyte and additionally also blood pigment separation properties despite this opening effect of the swelling agent. The swelling properties should be so good that for a test in which the rate of color formation—such as for example of a glucose test reaction—is mainly dependent on the penetration of the sample liquid through the layer, the optically detectable reaction is measurable after a maximum of one minute. Especially suitable swelling agents have proven to be methyl vinyl ether maleic acid anhydride copolymer, xanthan gum and methyl vinyl ether maleic acid copolymer. It will be understood that one or more detection layers may be used in accordance with the diagnostic test element of the present invention.

According to the invention the second layer should scatter light very strongly. Ideally the refractive index of the pigments in the second film layer should be at least 2.5. Hence $TiO_2$ is typically added to the layer. Thus, in an aspect of the diagnostic test element of the present invention, the said at least one separation layer further comprises $TiO_2$. In a typical aspect, the said $TiO_2$ is present in an amount of about 5.5 to 9.0 $g/m^2$. More typically, the separation layer may comprise $TiO_2$ in an amount of about 5.5 to 6.0 $g/m^2$, 5.5 to 6.5 $g/m^2$, 5.5 to 7.0 $g/m^2$, 5.5 to 7.5 $g/m^{2'}$ 5.5 to 8.0 $g/m^2$ or 5.5 to 8.5 $g/m^2$ or about 6.0 to 9.0 $g/m^2$, 6.5 to 9.0 $g/m^2$, 7.0 to 9.0 $g/m^2$, 7.5 to 9.0 $g/m^2$, or 8.0 to 9.0 $g/m^2$ or 8.5 to 9.0 $g/m^2$ or about 8.0 to 8.3 $g/m^2$, 7.5 to 8.0 $g/m^2$, 7.0 to 8.3 $g/m^2$, 6.5 to 8.3 $g/m^2$, or 6.0 to 8.3 $g/m^2$. In some embodiments the separation layer shall comprise $TiO_2$ in an amount of about 6.0 to 8.0 $g/m^2$. In some embodiments the separation layer shall comprise $TiO_2$ in an amount of about 7.0 to 8.0 $g/m^2$. In some embodiments the separation layer shall comprise $TiO_2$ in an amount of about 7.5 $g/m^2$. Moreover, it is envisaged that the said $TiO_2$ is present in an amount forming a ratio of $SiO_2$ to $TiO_2$ of between about 0.11 to 0.29, more particular, a ratio of about 0.12 to 0.27, 0.14 to 0.25 or 0.16 to 0.20, and, more particular, a ratio of about 0.17, 0.18 or 0.19.

Further, the detection layer and separation layer are, in an aspect, essentially free of iron-containing oxidizing agents. In a typical aspect, said iron-containing oxidizing agent is potassium ferricyanide (III).

Advantageously, it has been found in the studies underlying the present invention that the level of dispersion of solid components in the separation layer influences the remission kinetic of diagnostic test elements. In order to minimize the said influence, it was found that a strong dispersion level reaching a saturated stage (plateau stage), i.e. a maximum level where no further increase in dispersion is possible, is suitable to minimize the differences between the remission kinetics of individual batches of test elements. However, increasing the level of dispersion of the solid components alone has the drawback that remission rates of more than 100% may be obtained, if low levels of analytes, such as 0 to 10 mg/dL glucose, shall be determined. Further the kinetic was also slowed down for high analyte levels in the case of glucose. It has been found that the aforementioned drawbacks can be prevented by including $SiO_2$ in an amount of about 1.0 to 1.6 $g/m^2$ to the separation layer. Using $SiO_2$ in the aforementioned amount results in a particular favorable remission of 90 to 98 Rem. %, even at low glucose concentrations of about 10 mg/dL. An even higher amount of $SiO_2$ results in reduced remission which in turn would produce less pronounced differences in remission between high glucose levels of, e.g., 600 mg/dL and low glucose levels of, e.g., 10 mg/dL. Advantageously, the aforementioned favorable remission results from the inclusion of the $SiO_2$ as well as from the high degree of dispersion of the solid components since using $SiO_2$ alone also yields less favorable remission. Further improvements can be obtained by avoiding potassium ferricyanide (III) as an oxidizing agent in the detection layer and the separation layer as well as by adding phosphoromolybdic acid layer as an indicator at a very late stage to the coating composition forming the detection layer and the to separation layer such that hydrolysis or degradation of the indicator will be prevented. Furthermore, it has been found that pH adjustment of the coating composition should be carried out prior to the addition of the indicator. Using the aforementioned modifications in the detection layer and the separation layer, it has been found that remission is comparable between different batches of diagnostic test elements, i.e. are within a tolerance of at most about +/−5%. Thus, thanks to the diagnostic test element of the present invention, it is no longer required to provide individual calibration curves for batches of diagnostic test elements since the said test element allows for the use of a general calibration curve for all batches (uni- or no-code test strips). Moreover, cost and production time intensive measures such as storing the calibration information on each diagnostic test element via a bar code or providing the test elements of a batch in form of a labeled magazine can be avoided.

The definitions and explanations of the terms made before apply mutatis mutandis for the embodiments described below.

In the following, particular embodiments of the diagnostic test element of the invention are specified:

In an embodiment of the diagnostic test element of the invention, said at least one separation layer further comprises $TiO_2$.

In a further embodiment of the said diagnostic test element, said $TiO_2$ is present in an amount of about 5.5 to 9.0 g/m².

In yet a further embodiment of the said diagnostic test element, said $TiO_2$ is present in an amount forming a ratio of $SiO_2$ to $TiO_2$ of about 0.11 to 0.29.

In another embodiment of the diagnostic test element of the invention, said detection layer and separation layer are essentially free of iron-containing oxidizing agents.

In a further embodiment of the said diagnostic test element, said iron-containing oxidizing agent is potassium ferricyanide (III).

In yet an embodiment of the diagnostic test element of the present invention, said dispersion-saturated solid components have been obtained by dispersing the solid components in a coating composition forming the separation layer until a maximum is reached such that no further increase in the amount of dispersed solid components can be observed (plateau stage).

The invention also relates to a coating composition being capable of forming a detection layer and separation layer on a diagnostic test element of the present invention described above.

The term "coating composition" as used herein refers to a composition, typically an aqueous composition, which is capable of forming the separation layer comprised by the test field of the diagnostic test element. Typical components of the said separation layer are also contained in the coating composition. Moreover, the said composition will comprise suitable solvents for said components well known to the skilled artisan from, e.g., DE 196 29 657 A1, DE 196 29 656 A1, EP 0 821 234 B 1, EP 1 035 919 B1 or EP 1 035 920 B1 which are herewith incorporated by reference. In order to be capable of forming the separation layer of the diagnostic test element according to the preset invention, it is envisaged that the coating composition of the invention comprises silicic acid in an amount of about 2.0 g to 3.5 g per 100 g, more particular, an amount of about 2.1 g to 3.2 g per 100 g coating composition or an amount of about 2.1 g to 2.8 g per 100 g coating composition and, more particular, an amount of about 2.45 g per 100 g coating composition. In a typical aspect, said composition further comprises $TiO_2$ in an amount of about 11.0 g to 18.0 g per 100 g coating composition, more particular, an amount of about 12.0 g to 17.0 g per 100 g coating composition or an amount of about 13.0 g to 15.0 g per 100 g coating composition and, more particular, an amount of 13.6 g per 100 g coating composition.

Thus, in an embodiment of the coating composition of the invention, the coating composition of the invention comprises silicic acid in an amount of about 2.0 g to 3.5 g per 100g coating composition.

Moreover, in yet an embodiment of the coating composition of the invention, said composition further comprises $TiO_2$ in an amount of about 11.0 g to 18.0 g per 100 g coating composition.

The present invention also relates to a method for the manufacture of a diagnostic test element of the invention comprising dispersing solid components for the separation layer in a coating composition (preferably, a coating composition useful for forming the separation layer of the test field comprised by the diagnostic test element) until a maximum is reached such that no further increase in dispersed solid components occurs (plateau stage), wherein said coating composition comprises silicic acid in an amount of about 2.0 g to 3.5 g per 100g coating composition.

The method according to the present invention encompasses in an aspect the production of a coating composition being capable of forming the separation layer comprised in the test field of the diagnostic test element of the present invention. To this end, it is particularly envisaged that the solid components of the future separation layer are dispersed until a maximum is reached such that no further increase in dispersed solid components occurs (plateau stage). A further increase in dispersion of solid components will result in aggregation and/or sedimentation of said components. Accordingly, the maximum dispersion, i.e. the dispersion saturation, can be determined by the skilled artisan without further ado by, e.g., making a test series of dispersions of different degrees of saturation. Further components of the coating solution such as the silicic acid shall be dissolved such that a final amount of $SiO_2$ of about 1.0 to 1.6 g/m² can be achieved in the separation layer, e.g., in an amount of about 2.0 g to 3.5 g per 100 g coating composition.

In addition, $TiO_2$ may be dissolved in the composition in an aspect of the method of the invention, typically in an amount of about 11.0 g to 18.0 g per 100 g coating composition. In yet an aspect of the method, potassium ferricyanide as oxidizing agent shall be avoided. If phosphoromolybdic acid is used as an indicator in the separation layer, the said component shall be added at a rather late stage, e.g., not longer than 1 day prior to carrying out the coating process, of the production of the coating composition such that hydrolysis or degradation can be prevented. In an aspect the said phosphoromolybdic acid is added after the pH of the coating composition has been adjusted.

In a similar manner, the coating composition for the detection layer can be produced, i.e. by dispersion and dissolution of the necessary components. Components of the coating solution forming the detection layer are those which are present in the detection as discussed elsewhere herein.

The manufacture of diagnostic test elements comprising test fields having a multiple layer structure is, in principle, well known to the person skilled in the art and described, e.g., in DE 196 29 657 A1, DE 196 29 656 A1 or EP 0 821 234 B1 which are herewith incorporated by reference. In an aspect, a coating composition for the detection layer is applied to the test field on the diagnostic element first. Subsequently, the solvent is removed from the coating composition resulting in the formation of a dry first layer, i.e. the detection layer. In a further step, the coating composition for the separation layer is applied to the first layer. The solvent is again removed in order to generate the second layer, i.e. the separation layer. The solvent can be removed from the coating composition after application of the said composition to the test field of the diagnostic test element by all techniques known for removing solvents including heat treatment, evaporation or freeze-drying.

In an embodiment of the method of the present invention, said method further comprises adding phosphoromolybdic acid as indicator to the coating composition.

In a particular embodiment of the method, it is envisaged that said phosphoromolybdic acid is added less than 2 days, less than 1 day, less than 6 hours, less than 3 hours, less than 2 hours or less than 1 hour prior to applying the coating composition to the test field of the diagnostic test element.

In yet an embodiment of the aforementioned methods, said phosphoromolybdic acid is added after pH adjustment of the coating composition.

The present invention also pertains to a method for determining the presence or amount of an analyte in a body fluid sample.

Such a method may typically comprise the steps of:
(a) contacting the diagnostic test element of the invention with a body fluid suspected to comprise the analyte under conditions suitable for allowing detection of the analyte by the detection reagent(s) comprised in the detection layer;
(b) measuring a change in at least one optical property of the indicator reagent in the wetted layers on the diagnostic test element, whereby the presence or amount of the analyte in the body fluid sample will be determined.

Contacting as used herein means that the body fluid sample is applied to the carrier in a manner as to allow for physical contact of the composition of the invention comprised by the carrier and the body fluid sample. In particular, contacting is carried out for a time and under conditions being sufficient for allowing the detection reagent(s) to become activated. For example, if glucose is to be determined as analyte, the glucose dehydrogenase shall be reconstituted, i.e. wetted and dissolved, and, thus, become biologically active. Suitable conditions depend on the diagnostic carrier and are known in the art. The body fluid sample that can be applied to the test element, in an aspect, may have a volume of less than 2 microliters, more particularly of less than 1 microliter.

Upon activation of the detection agent(s), e.g., reconstitution of the biologically active dehydrogenase, the agent shall bind to its substrate, i.e. the analyte comprised in the body fluid sample, and inducing a detectable change such as a conversion of the substrate into a respective product and redox equivalents. The redox equivalents generated by, e.g., the dehydrogenase allow for determining the dehydrogenase activity since the redox equivalents generated by the enzymatic conversion catalyzed by the dehydrogenase are transferred by the agent capable of eliciting a change in at least one optical property of the indicator in the presence of redox equivalents in the composition comprised to the indicator reagent. The change in the at least one optical property of the indicator can than be measured. Depending on the diagnostic test element, the measurement of the change of the optical property can be achieved by different techniques known in the art. For detecting the change of an optical property such as color, a spatially resolving optical detector may be used. A spatially resolving optical detector is to be understood to mean an optical detector which has a multiplicity of optical sensors which are able to record regions of the detection side of the detection layer which are not completely congruent. More particularly, the spatially resolving optical detector can comprise at least one image sensor, i.e., an array of optical detectors which can be one-dimensional or else two-dimensional. More particularly, the optical detector can thus comprise a CCD chip and/or CMOS chip. In addition, the spatially resolving optical detector can comprise at least one optical element for imaging the detection side and/or the detection layer onto an image-sensitive surface of the spatially resolving optical detector.

A change in at least one optical property measured by the method described above shall be indicative for the presence of the analyte. It will be understood by the skilled artisan that in order to determine the amount of an analyte, it might be necessary to compare the extent of the change of the optical property. To this end, it might be, furthermore, necessary to compare a detected signal accompanying the optical change to signals accompanying optical changes elicited by known amounts of analytes, i.e. calibration signals. How such a calibration can be established is well known to the skilled artisan.

In light of the above, the invention contemplates, in general, the use of the diagnostic test element of the invention for determining the amount of an analyte, preferably, glucose, in a sample of a subject.

Based on the determination of the amount of the analyte, it may be assessed whether a subject, e.g., a human, suffers from a disease or has a predisposition therefor. If the analyte is glucose, the diagnostic test element may be, thus, used for aiding the diagnosis of diabetes or other diseases or disorders with impaired glucose metabolism.

All references cited in this specification are herewith incorporated by reference with respect to their entire disclosure content and the disclosure content specifically mentioned in this specification.

FIGURES

FIG. 1 shows remission kinetics at different blood glucose amounts (0 mg/dl blood (A); 10 mg/dl blood (B); 60 mg/dl blood (C); 120 mg/dl blood (D); 300 mg/dl blood (E); 600 mg/dl blood (F)) for different coating compositions. Squares=MIC; triangles dark=NoCode without OAF, without K3, dispersed; light triangles=NoCode with OAF, without K3; diamonds=NoCode without OAF, with K3; cross=MIC with OAF with K3.

EXAMPLES

Figure 1:
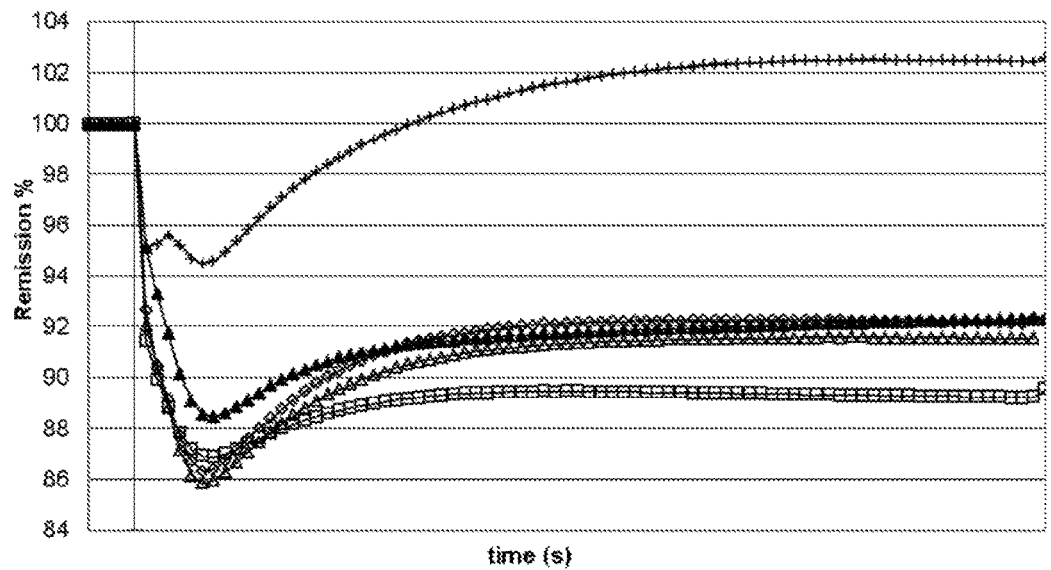
Figure 1:
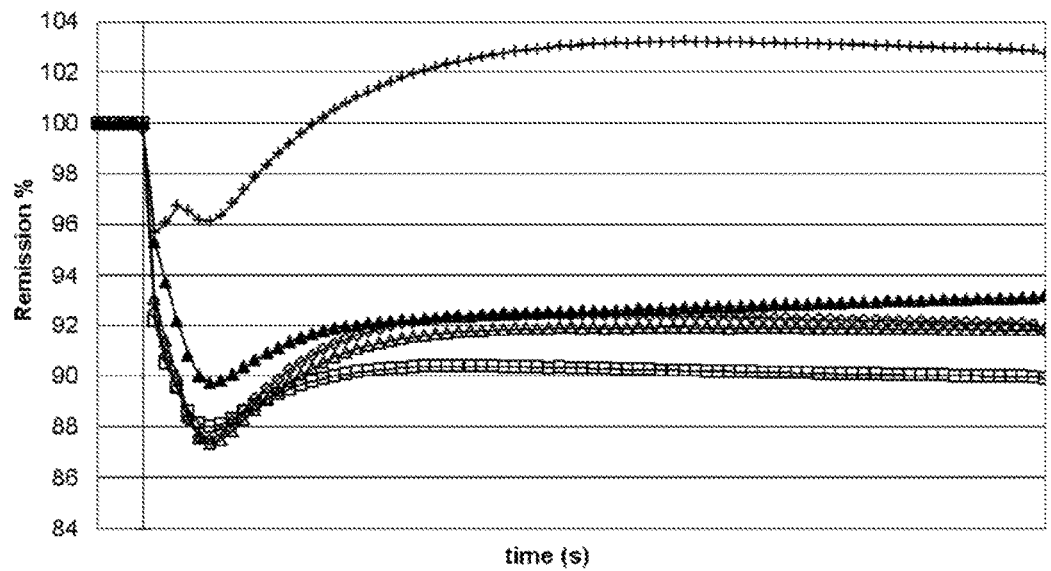
Figure 1:
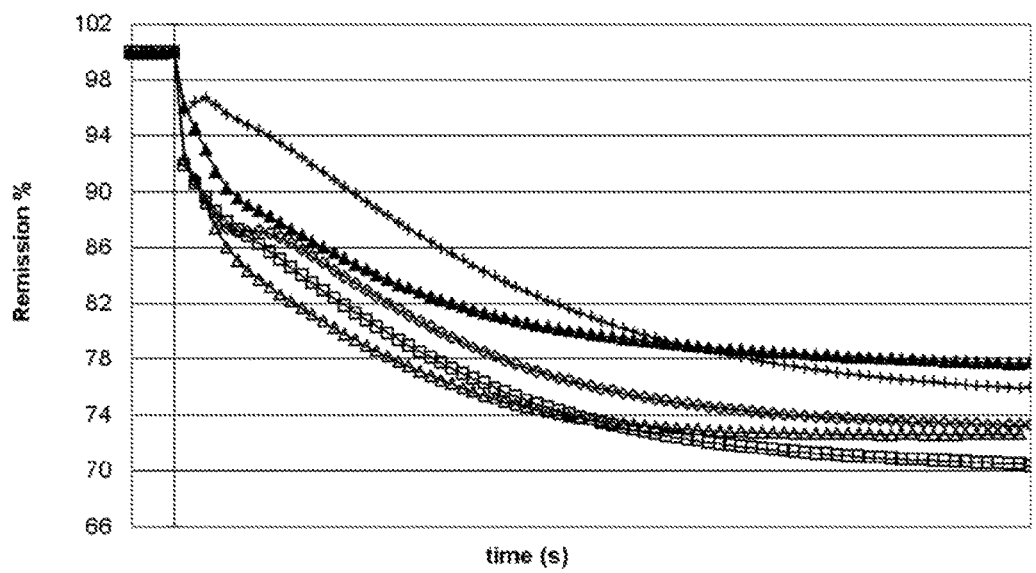
Figure 1:
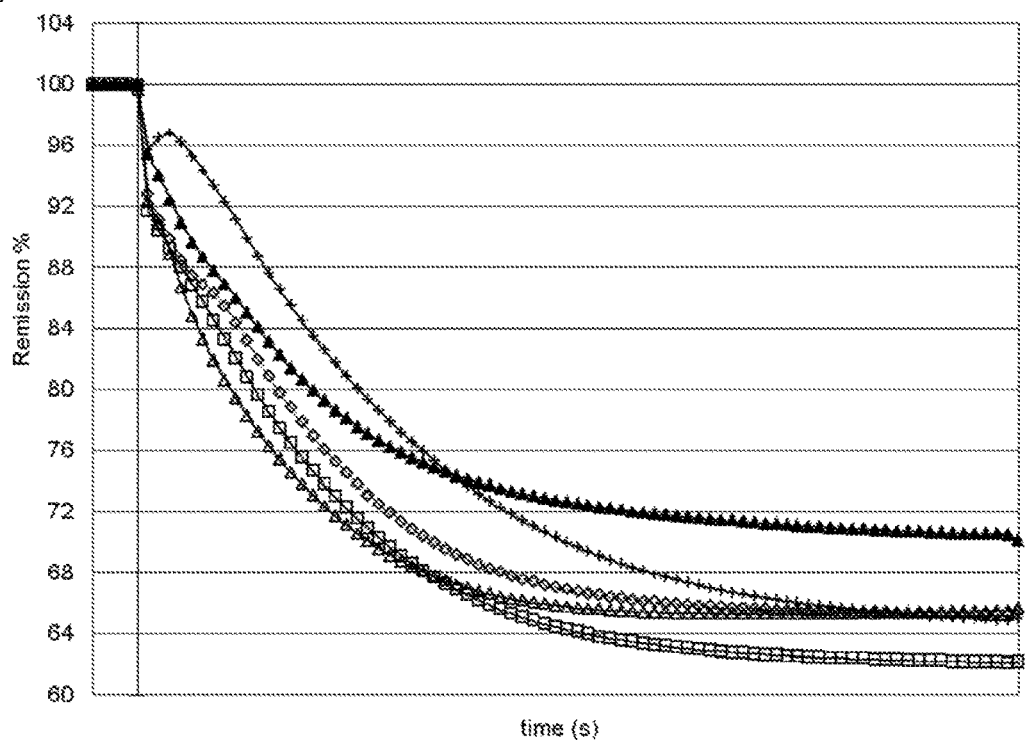
Figure 1:
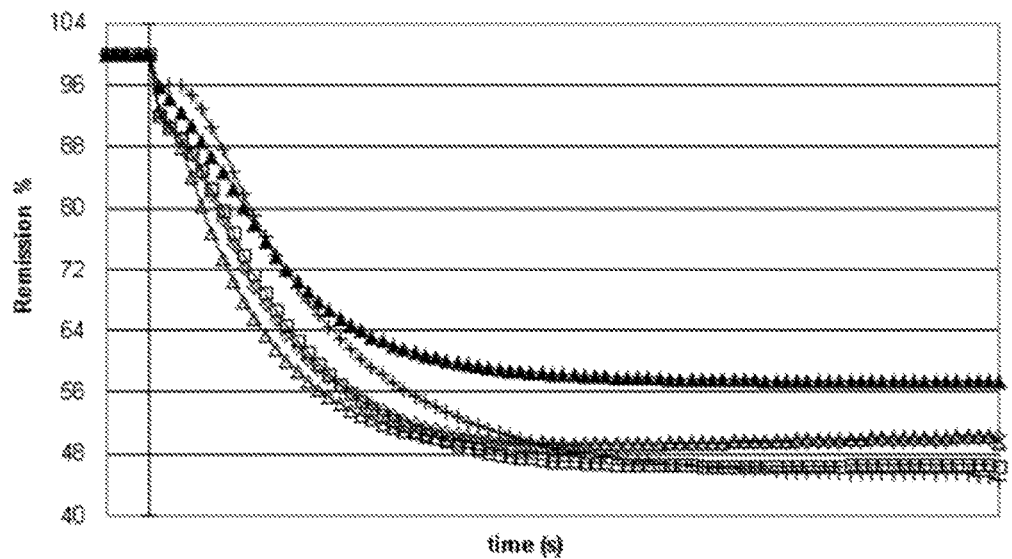
Figure 1:
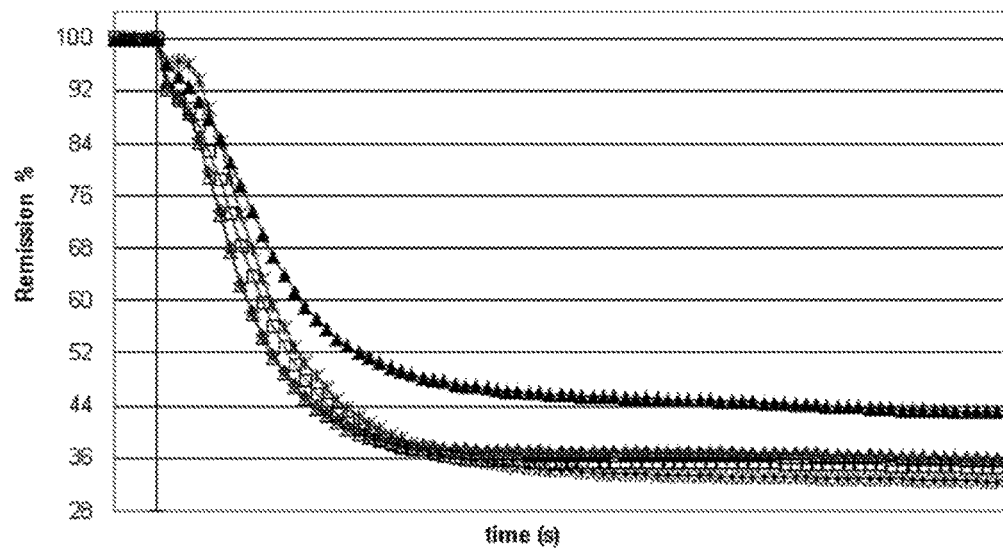

The following Examples shall merely illustrate the invention or aspects thereof. They must, however, not be construed in any way which limits the scope of the invention.

Example 1

Manufacture of a Diagnostic Test Element

TABLE 1

Components of the improved coating composition (MIC-NoCode) for the first layer compared to a conventional coating composition (MIC)

| | First layer | |
|---|---|---|
| components | MIC-No-Code amounts for the coating composition | MIC amounts for the coating composition |
| L-Glycerol-3-Phosphate-disodium salt | 1.0 g | 1.0 g |
| Calciumchloride-2-hydrate | 0.05 g | 0.05 g |
| Xanthan gum | 0.4 g | 0.4 g |
| Tetraethylammoniumchloride | 0.05 g | 0.05 g |
| M-Octanoyl-N-methyl-glucamide | 0.2 g | 0.2 g |
| Polyvinylpyrrolidone (MG 25000) | 1.0 g | 1.0 g |
| Sodium-Aluminum silicate | 5.7 g | 5.7 g |
| Polyvinylpropionate-dispersion (50% (w/w) in water) | 5.6 g | 5.6 g |
| Bis-(2-hydroxyethyl)-(4-hydroximinocyclohexa-2,5-dienylidin)-ammoniumchloride | >0.08 g | >0.08 g |
| 2,18-Phosphormolybic acid-hexasodium salt | >0.23 g | >0.23 g |
| Mutant of the Chinoproteine glucosedehydrogenase (Mut. Q-GDH, EC 1.1.5.2) from Acinetobacter spec. | >0.4 KU | >0.4 KU |
| Pyrrolochinollin-chinone | 0.002 g | 0.002 g |
| Water | 85 g | 85 g |

The components for the first layer were admixed in the amounts indicated in Table 1, pH was adjusted at 6.75 and the composition was applied at a coating weight per unit are of 75 g/m².

TABLE 2

Components of the improved coating composition (MIC-NoCode) for the second layer compared to a conventional coating composition (MIC)

| | Second layer | |
|---|---|---|
| components | MIC-No-Code amounts for the coating composition | MIC amounts for the coating composition |
| Sodium hydroxide | 0.25 g | 0.35 g |
| Gantrez ® (Methylvinylether-maleic acid copolymere) | 1.0 g | 1.4 g |
| M-Octanoyl-N-methyl-glucamide | 0.25 g | 0.33 g |
| Tetraethylammoniumchloride | 0.4 g | 0.52 g |
| Polyvinylpyrrolidone (MG 25000) | 1.4 g | 1.8 g |
| Titandioxide | 13.6 g | 17.9 g |
| Precipitated silicic acid | 2.5 g | 1.9 g |
| Polyvinylpropionate-dispersion (50% (w/w) in water) | 4.4 g | 5.7 g |
| Bis-(2-hydroxyethyl)-(4-hydroximinocyclohexa-2,5-dienylidin)-ammoniumchloride | >0.04 g | 0.08 g |
| 2,18-Phosphormolybdic acid-hexasodium salt | >1.4 g | 2.3 g |
| Water | 74 g | 67 g |

The components for the first layer were admixed in the amounts indicated in Table 1, pH was adjusted at 6.75 and the composition was applied at a coating weight per unit are of 50 g/m².

Using the above mentioned coating compositions as first and second layer coating compositions, the manufacture of diagnostic test elements was carried out essentially as described in DE 196 29 657 A1, DE 196 29 656 A1 or EP 0 821 234 B1.

Example 2

Influence of Dispersion Degree of Solid Components and SiO₂ in the Second Layer on Remission Blood glucose was measured at different concentrations (i.e. 0, 10, 60, 120, 300 and 600 mg/dl blood) using the diagnostic test elements having different coatings in order to determine the influence on several parameters on standard (MIC) and NoCode coating systems in an Accu-Chek-Active MIC assay. The following combinations were measured:

MIC with potassium ferricyanide (K3);
NoCode with K3
NoCode without K3
NoCode without K3 dispersed As is evident from the diagrams presented in FIG. 1, different degrees of dispersion resulted in different remissions. Since the dispersion is usually varying from batch to batch, the aforementioned effect of the dispersion degree in a test element requires the use of batch specific calibration. In order to minimize the influence of the dispersion degree on remission, a further coat has been used with highly dispersed (i.e., in the saturation stage) solid components (OAF).

MIC with OAF and with K3

However, using this coat, remission rates at low glucose concentrations (e.g., 0-10 mg/dl glucose in the blood) exceeded 100% such that the evaluation with the calibration curve was no longer possible. Moreover, remission kinetics was slowed down significantly; see FIG. 1.

The high dispersion degree in the coating composition also resulted in a reduced porosity in the dry coat such that the optical density was increased. This results in an increase of the remission in low or 0 mg/dl-blood glucose samples as mentioned before. Moreover, diffusion velocity into the coat of the glucose was diminished. These effects have been further validated by absorption capacity measurements of different coatings, i.e. NoCode without K3 and NoCode without K3, dispersed; see FIG. 2.

Figure 2:
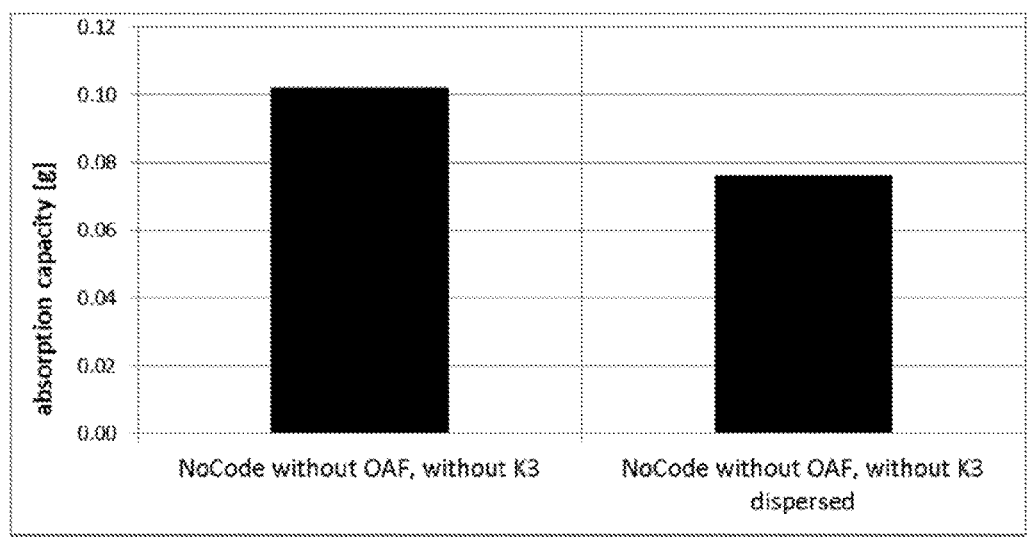
FIG. 2 shows a reduction in absorption capacity (A) and velocity (B) for coating composition NoCode without OAF, without K3 dispersed vs. non-dispersed.
Figure 2:
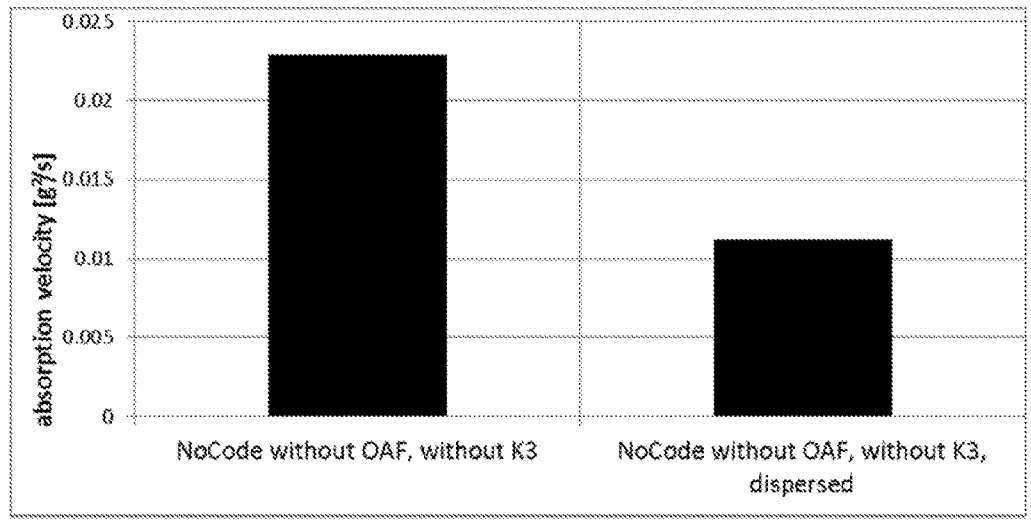

The absorption capacity was reduced by about 25% and the diffusion velocity by about 50%; see FIG. 2.

In order to avoid the undesired increase in remission when measuring low levels of blood glucose and in order to improve the kinetics, the amount of $SiO_2$ in the second layer was increased by about 70% from about 0.7 $g/m^2$ to a final amount of 1.0 to 1.6 $g/m^2$. In test elements having such second layers, particular well suited remission ranges of 90 to 98 remission % could be generated. It has been, furthermore, found that a further increase in $SiO_2$ results in reduced remission such that the differences in remission between low concentration samples and high concentration samples are less pronounced such that the measurement system as such would become less precise.

Moreover, it was found that using the superior $SiO_2$ concentration in the second layer without the increased dispersion degree also results in a reduction of remission and a strong dependency on the relative humidity during the measurement. Accordingly, the increased dispersion degree and the increase of $SiO_2$ in the second layer should be used in combination in order to improve a test element with respect to batch independent calibration.

Example 3

Influence of Phosphomolybdic Acid and Potassium Ferricyanide on Remission

It was further found that the phosphomolybdic acid shall stay in the coating composition as short as possible in order to avoid interference with the later measurement. Moreover, it was found that NaOH used for making pH adjustments of the coating composition shall be added prior to the addition of the phosphomolybdic acid in order to avoid hydrolysis. The production of the coating composition was amended accordingly. However, even in this case, it was found that the calibration code curves were sigmoidal which makes the differentiation between high and low blood glucose concentrations difficult. Moreover, the time of measurement was also found to be increased.

Figure 3:
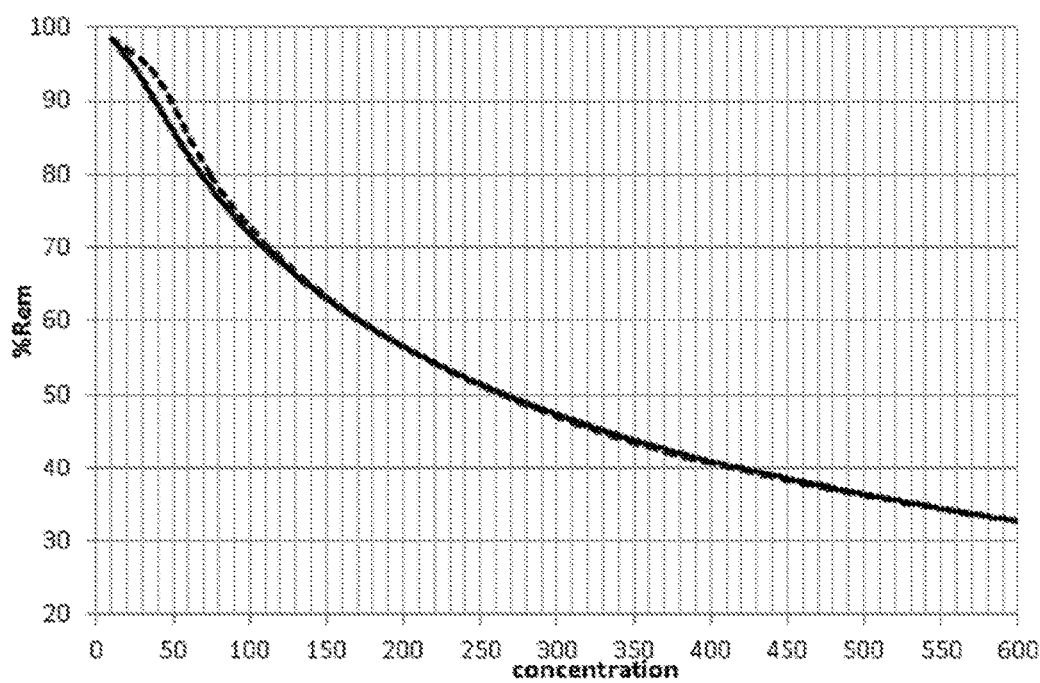
FIG. 3 shows linear relationship at low concentrations of glucose with % remission. Dotted line=NoCode with OAF, with K3; permanent line=NoCode with OAF, without K3.

It was found that the aforementioned aspects were caused by potassium ferricyanide (III) (K3) and that the negative effects could be overcome by avoiding the said K3 in both layers of the test element; see FIG. 3.

Figure 4:
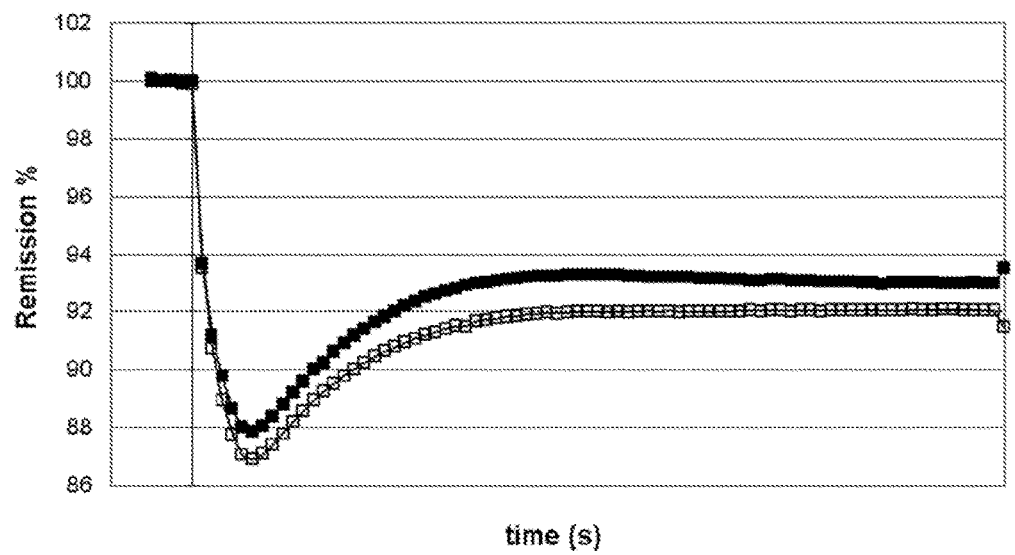
FIG. 4 shows remission kinetics at different blood glucose amounts (0 mg/dl blood (A); 10 mg/dl blood (B); 45 mg/dl blood (C); 120 mg/dl blood (D); 300 mg/dl blood (E); 600 mg/dl blood (F)) for different coating compositions. Light Squares=NoCode with OAF and plus $SiO_2$, without K3; dark squares=NoCode with OAF and plus SiO2, with K3.
Figure 4:
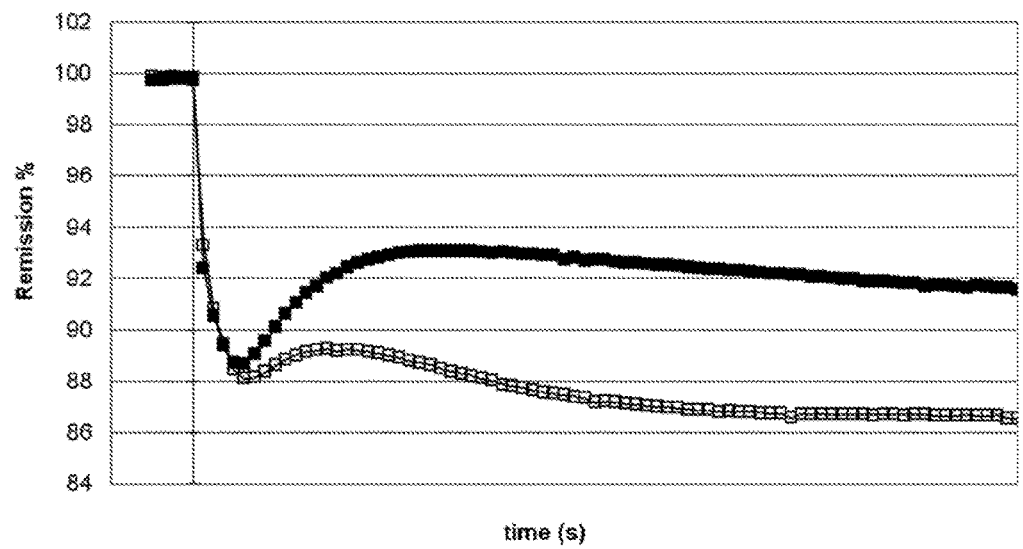
Figure 4:
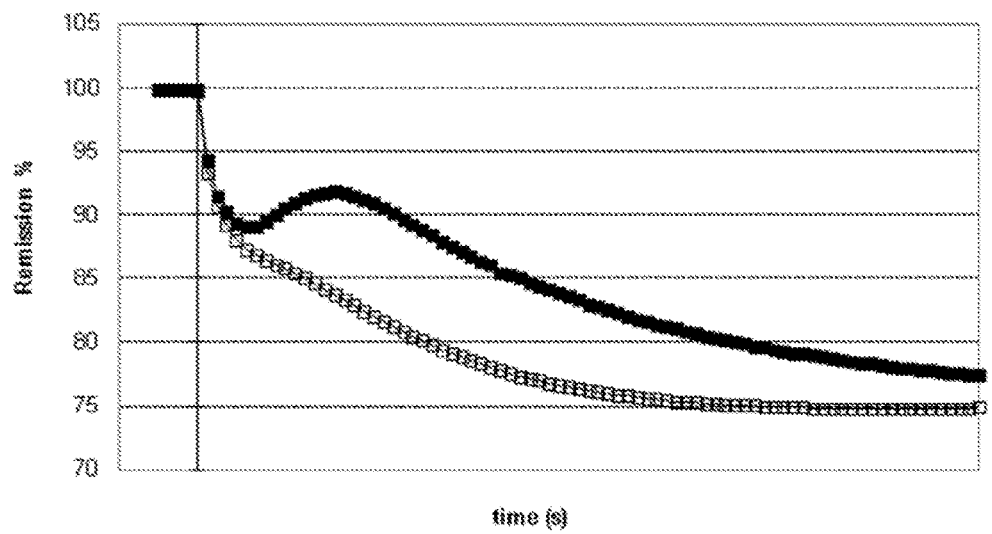
Figure 4:
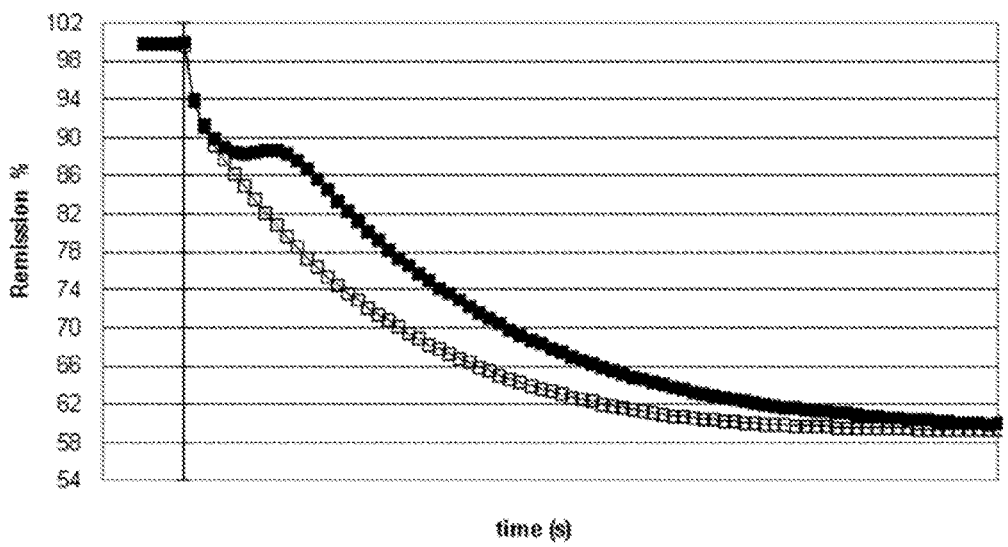
Figure 4:
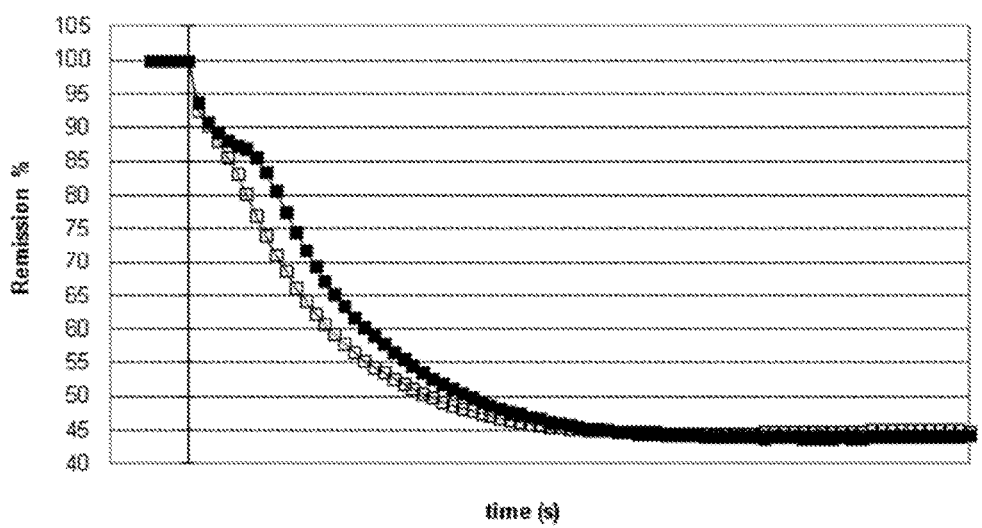
Figure 4:
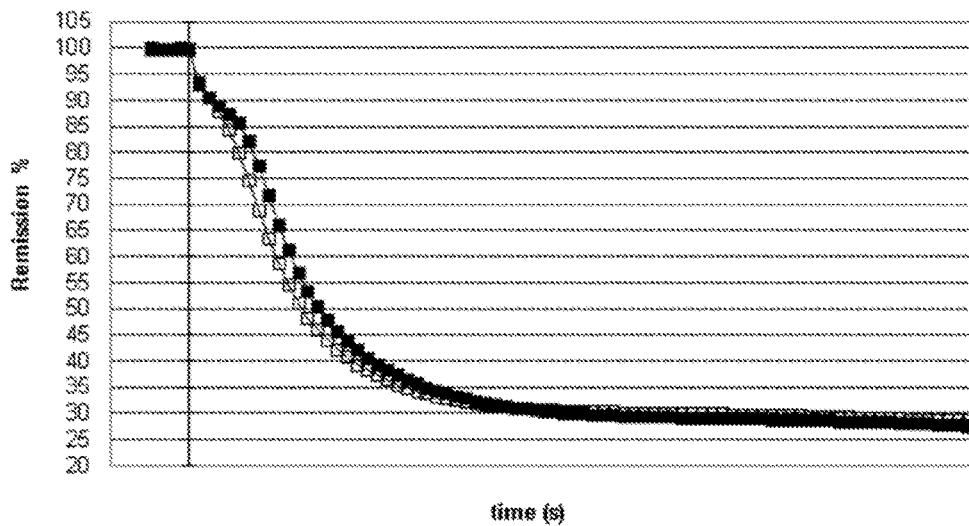

A further side effect of avoiding K3 was that the kinetics of remissions, in particular when measuring concentrations in the middle range of, e.g. 45 to 120 mg/dl glucose in blood, were significantly faster; see FIG. 4.

Figure 5:
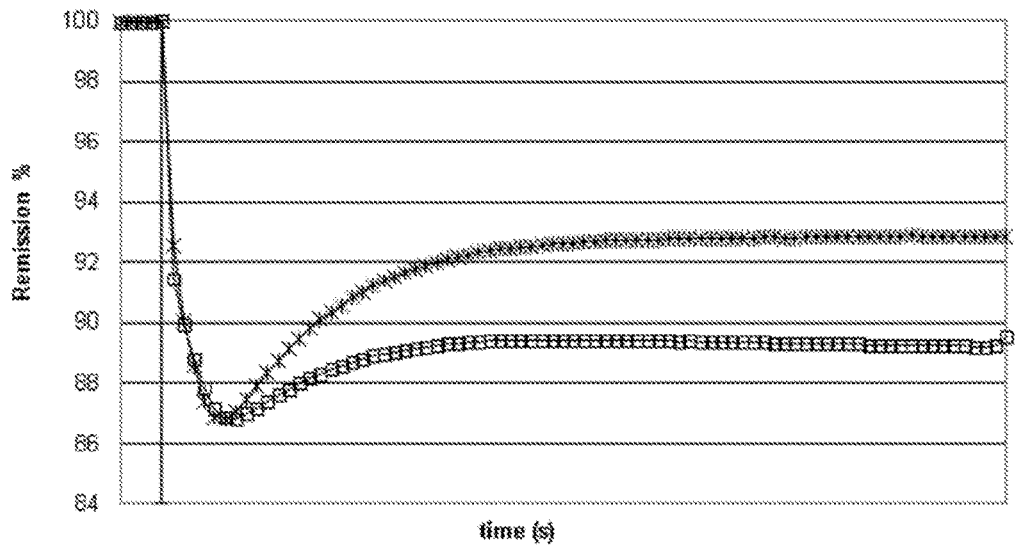
FIG. 5 shows remission kinetics at different blood glucose amounts (0 mg/dl blood (A); 10 mg/dl blood (B); 60 mg/dl blood (C); 120 mg/dl blood (D); 300 mg/dl blood (E); 600 mg/dl blood (F)) for different coating compositions. squares=MIC (without OAF, with K3); cross=NoCode with OAF and plus SiO2, without K3.
Figure 5:
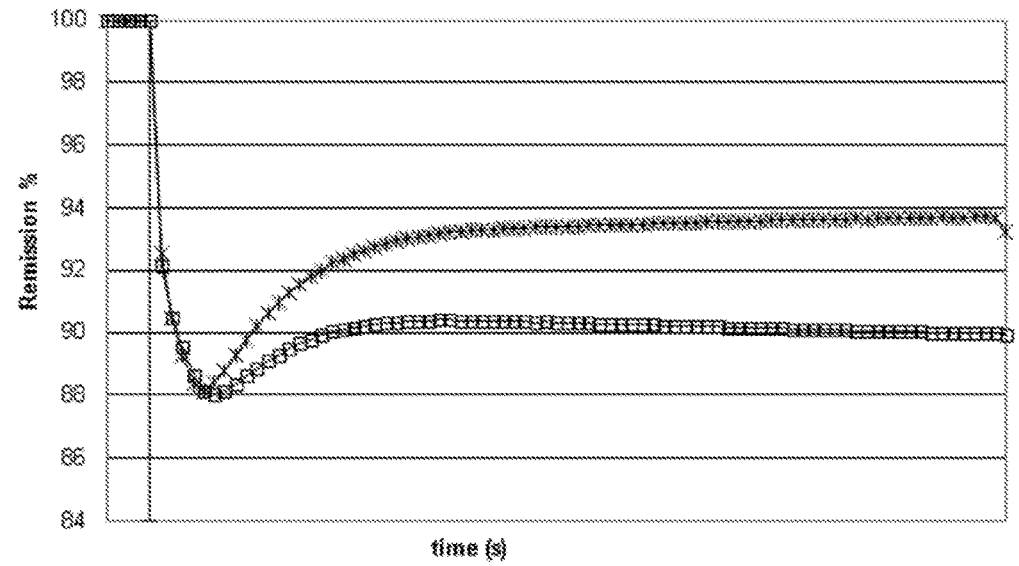
Figure 5:
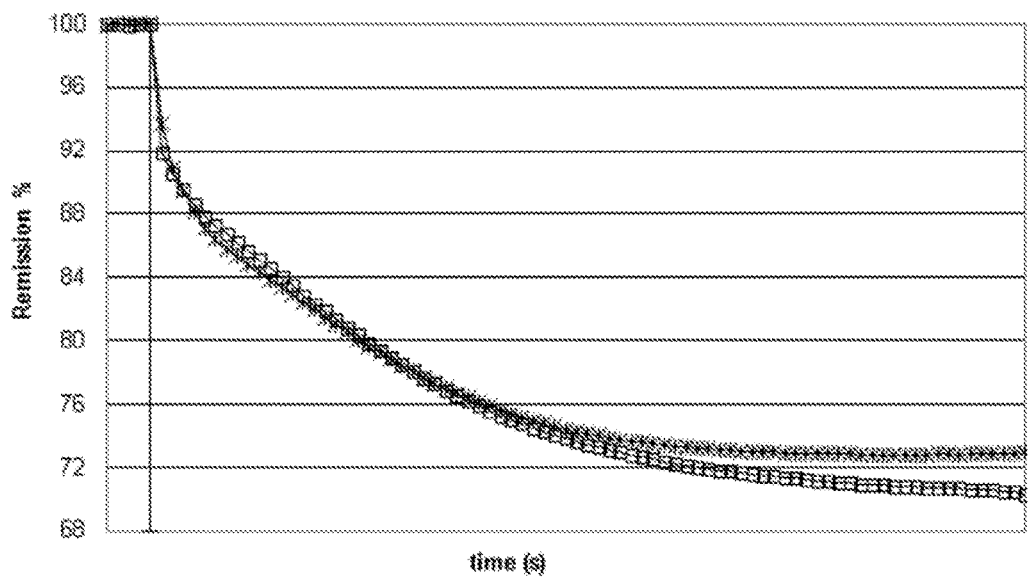
Figure 5:
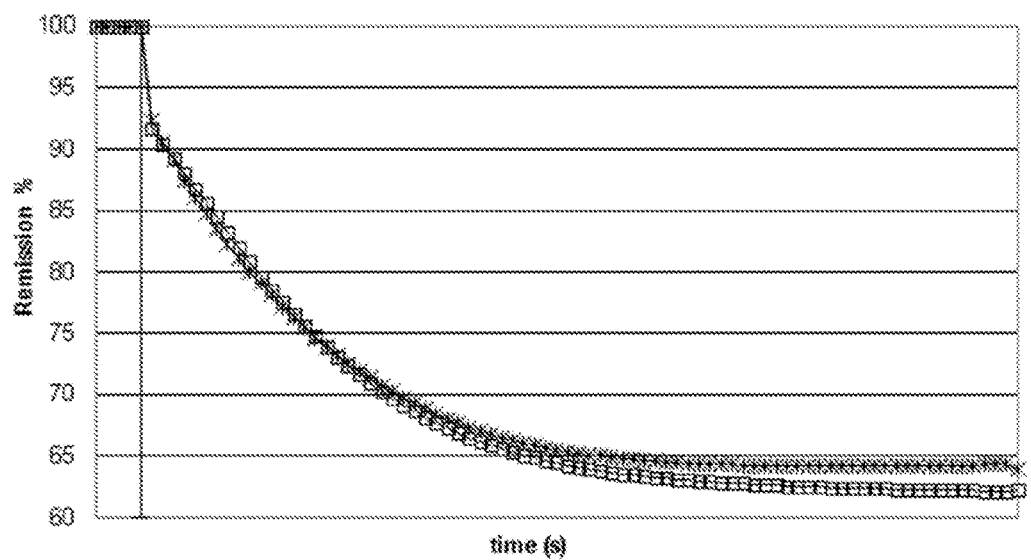
Figure 5:
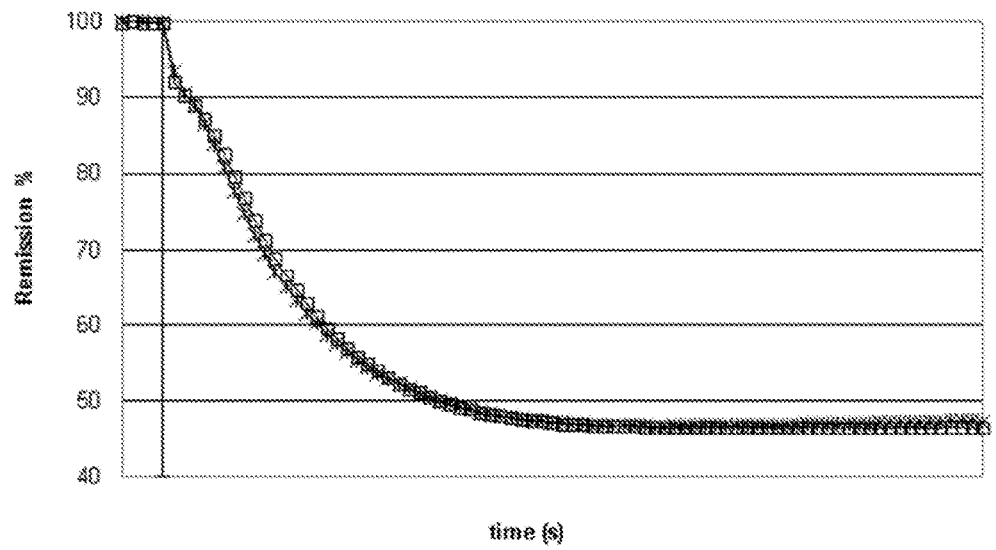
Figure 5:
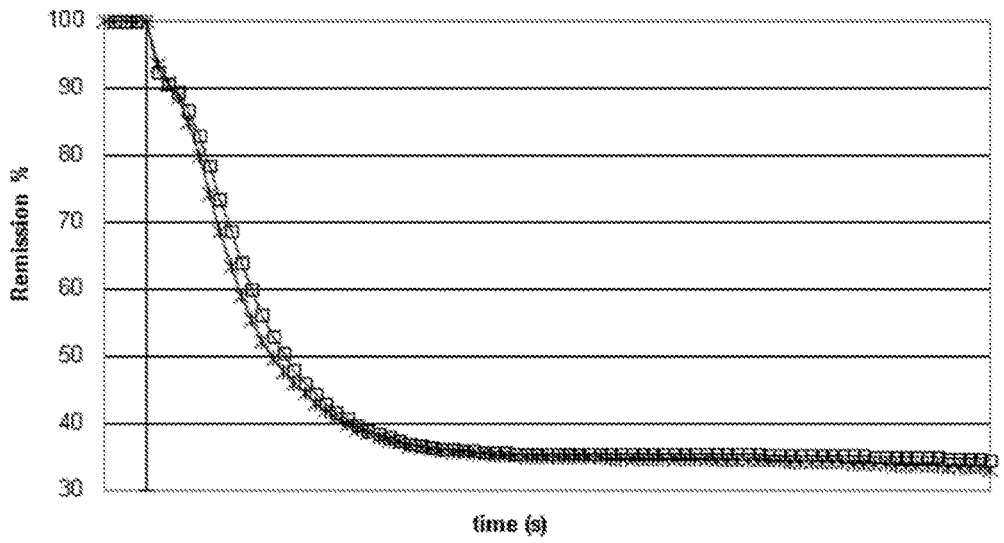

In FIG. 5, the improvements made in accordance with the present invention, i.e. NoCode with OAF and plus $SiO_2$, without K3, are summarized and compared with the standard MIC without OAF with K3.

Figure 6:
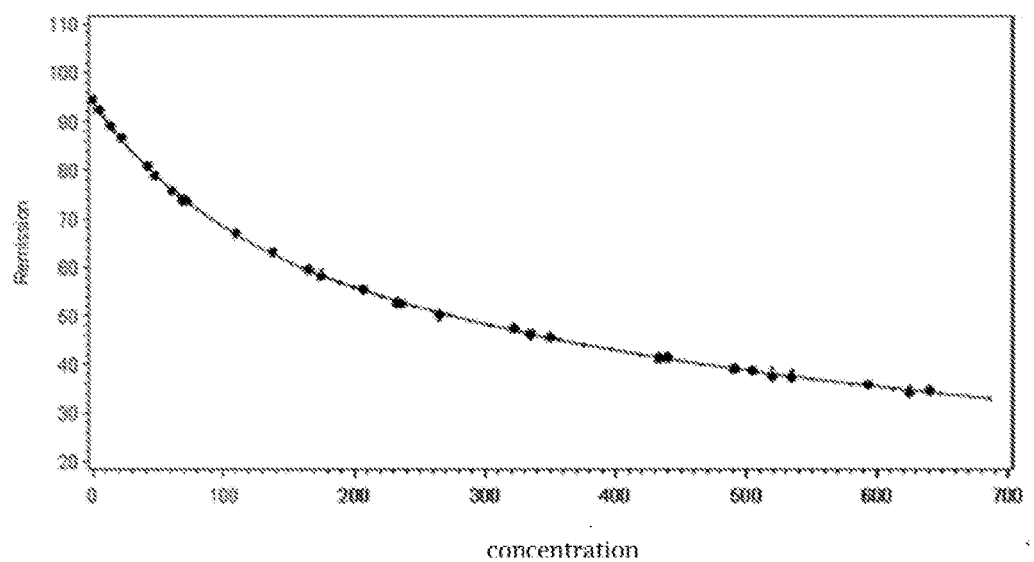
FIG. 6 shows a calibration Unicode curve for NoCode with OAF and plus SiO2, without K3 (A). The precision for the measurement is shown in (B).
Figure 6:
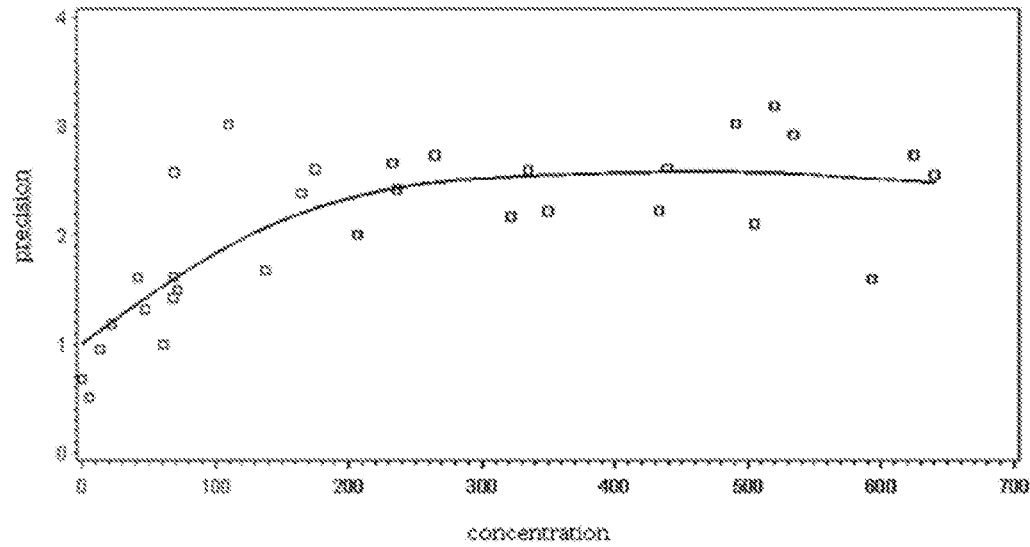

FIG. 6 A shows that a linear decreasing calibration curve can be obtained. There is enough remission at low glucose concentration and a suitable difference between high and low glucose concentrations resulting in good precision and low variability.

FIG. 6 B shows the precision of the improved test element.

The invention claimed is:

1. A diagnostic test element for determining an analyte comprised in a body fluid sample, said test element comprising at least one test field with at least one detection layer and at least one separation layer, wherein said at least one separation layer comprises $SiO_2$ in an amount of 1.0 to 1.6 $g/m^2$ and dispersion-saturated solid components,
   wherein said dispersion-saturated solid components have been obtained by dispersing the solid components in a coating composition forming the separation layer until a maximum is reached such that no further increase in the amount of dispersed solid components can be observed (plateau stage).

2. The diagnostic test element of claim 1, wherein said at least one separation layer further comprises $TiO_2$.

3. The diagnostic test element of claim 2, wherein said $TiO_2$ is present in an amount of 5.5 to 9.0 $g/m^2$.

4. The diagnostic test element of claim 2, wherein said $TiO_2$ is present in an amount forming a ratio of $SiO_2$ to $TiO_2$ of 0.11 to 0.29.

5. The diagnostic test element of claim 1, wherein said detection layer and separation layer are essentially free of iron-containing oxidizing agents.

6. The diagnostic test element of claim 5, wherein said iron-containing oxidizing agent is potassium ferricyanide (III).

7. A coating composition being capable of forming a separation layer on a diagnostic test element as described in claim 1.

8. The coating composition of claim 7, wherein said composition comprises silicic acid in an amount of 2.0 g to 3.5 g per 100 g coating composition.

9. The coating composition of claim 7, wherein said composition further comprises $TiO_2$ in an amount of 11.0 g to 18.0 g per 100 g coating composition.

10. A method for the manufacture of a diagnostic test element according to claim 1 comprising dispersing solid components for the separation layer in a coating composition until a maximum is reached such that no further increase in dispersed solid components occurs (plateau stage), wherein said coating composition comprises silicic acid in an amount of 2.0 g to 3.5 g per 100 g coating composition.

11. The method of claim 10, wherein said method further comprises adding phosphoromolybdic acid as indicator to the coating composition.

12. The method of claim 11, wherein said phosphoromolybdic acid is added less than 2 days, less than 1 day, less than 6 hours, less than 3 hours, less than 2 hours or less than 1 hour prior to applying the coating composition to the test field of the diagnostic test element.

13. The method of claim 11, wherein said phosphoromolybdic acid is added after pH adjustment of the coating composition.

* * * * *